United States Patent [19]

Marsoner et al.

[11] Patent Number: 5,193,545
[45] Date of Patent: Mar. 16, 1993

[54] DEVICE FOR DETERMINING AT LEAST ONE MEDICAL VARIABLE

[75] Inventors: Hermann Marsoner, Steinberg; Falko Skrabal; Helmut List, both of Graz, all of Austria

[73] Assignee: AVL Medical Instruments AG, Schaffhausen, Switzerland

[21] Appl. No.: 476,360

[22] Filed: Feb. 7, 1990

[30] Foreign Application Priority Data

Feb. 8, 1989 [AT] Austria .................................... 271/89

[51] Int. Cl.⁵ ............................................... A61B 5/00
[52] U.S. Cl. ........................... 128/635; 128/DIG. 13; 604/27; 604/48
[58] Field of Search ....... 128/632, 635, 637, DIG. 13; 604/27, 28, 48-50

[56] References Cited

U.S. PATENT DOCUMENTS

| | | | |
|---|---|---|---|
| 3,707,967 | 1/1973 | Kitrilakis et al. | 604/29 |
| 3,757,771 | 9/1973 | Ruegg et al. | 128/635 |
| 4,274,417 | 6/1981 | Delpy | 128/632 |
| 4,516,580 | 5/1985 | Polanyi | 128/632 |
| 4,585,007 | 4/1986 | Uchigaki et al. | 128/632 |
| 4,774,955 | 10/1988 | Jones | 128/632 |
| 5,097,834 | 3/1992 | Skrabal | 128/632 |

Primary Examiner—Lee S. Cohen
Assistant Examiner—K. M. Pfaffle
Attorney, Agent, or Firm—Watson, Cole, Grindle & Watson

[57] ABSTRACT

A device designed for determining one or more medical variables in living organisms, comprises a part to be inserted into the tissue of the organism, which has an exchange channel with openings into the tissue. The device comprising a delivery unit connected with the exchange channel for the delivery of a perfusion fluid and its drainage after partial equilibration with the medical variable or quantity to be measured, i.e., preferably glucose concentration, and comparatively constant endogenous or exogenous marker variables. The device further comprising an analyzing unit for measuring the medical variable and one marker variable, and an evaluation unit for determining the actual concentration of the medical variable with the use of the marker variables. The proposal is put forward that the part to be inserted into the tissue is configured as a flexible plastic cannula, and that this cannula is provided with a puncturing needle on one end, and that the two ends of the cannula are connected to feeder and drainage tubes of the delivery unit both on the pressure and suction side.

9 Claims, 2 Drawing Sheets

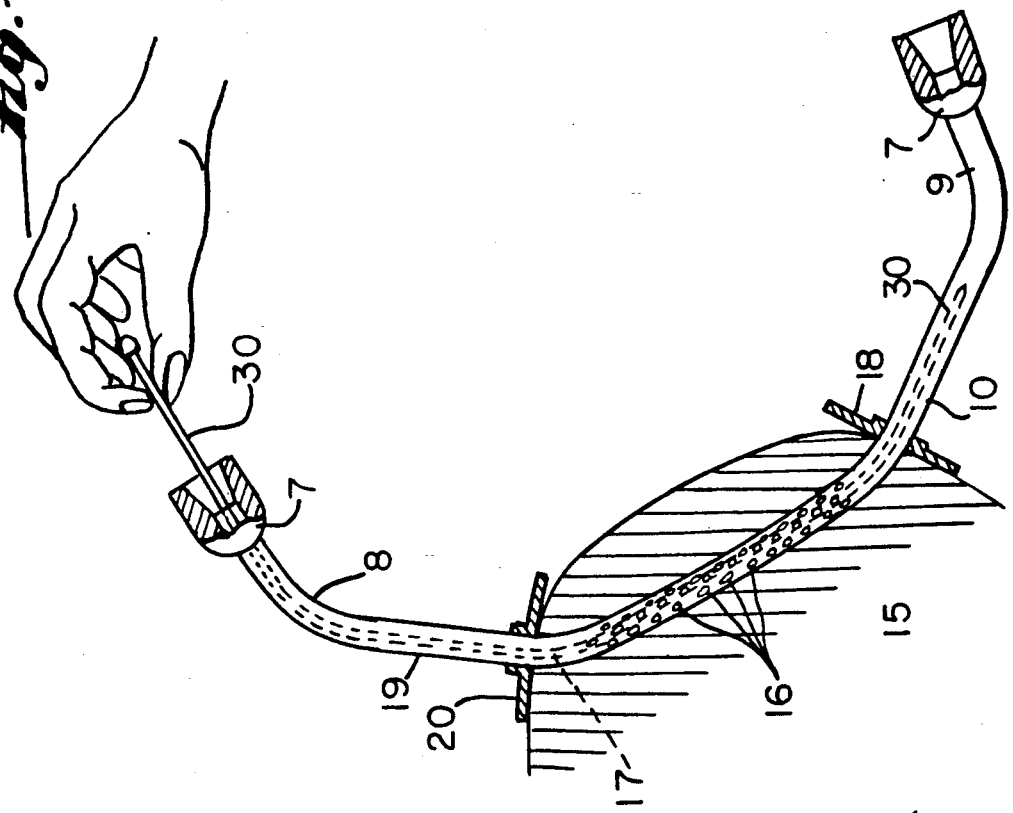
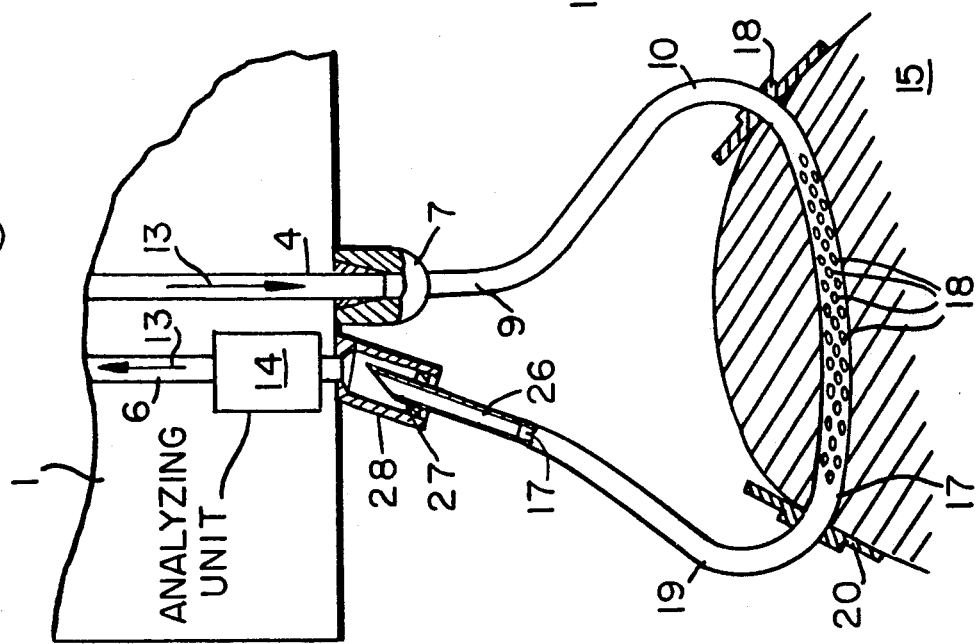

DEVICE FOR DETERMINING AT LEAST ONE MEDICAL VARIABLE

BACKGROUND OF THE INVENTION

This invention relates to a device for determining one or more medical variables to be measured in living organisms, comprising a part to be inserted into the tissue of the organism, which has an exchange channel with openings into the tissue, and further comprising a delivery unit connected with the exchange channel for the delivery of a perfusion fluid and its drainage after partial equilibration with the medical variable, i.e., preferably glucose concentration, and comparatively constant endogenous or exogenous marker variables, and further comprising an analyzing unit for measuring the medical variable and one marker variable and an evaluation unit determining the actual concentration of the medical variable with the use of the marker variable.

DESCRIPTION OF THE PRIOR ART

In medical applications it is often necessary to analyze the composition of body fluids repeatedly or continuously so as to be able to detect and eliminate disturbances of the homeostasis. In order to render unnecessary frequent withdrawals of blood numerous attempts have been made over the years to place sensors in the patient's body in order to obtain a steady flow of information.

In this context the continuous determination of glucose concentrations in the human organism is of particular relevance. In U.S. Pat. Nos. 4,221,567, 4,253,456, and 4,516,580, for instance, methods and apparatus for dialysis are disclosed, in which at least one cannula or catheter is introduced into the bloodstream. By means of dialytic membranes a test fluid may be fully equilibrated with the blood and may then be tested for the medical variable, e.g. glucose concentration. The membranes, which are subject to the test fluid on one side and to the body fluids, such as blood, on the other side, and which must be sufficiently large to permit adequate equilibration, are soon contaminated or clogged by body substances, however, which will quickly impede the exchange of the substances of interest. As regards the foreign bodies introduced into the bloodstream, such as cannulas or catheters, there is constant danger of infection, thrombosis or embolism. Besides, there are only few blood vessels available for long-term therapy, which will soon become obstructed by clots, thus preventing further use of the method.

The above disadvantages are avoided by a device of the kind described at the beginning of this paper, which is presented in WO 88/05643. Inside the housing of this device there is a plunger pump with a reservoir for the perfusion fluid, which pump may be used both for displacing the perfusion fluid from the plunger chamber and for delivering it into the collecting vessel opening up behind the plunger. The perfusion fluid may be delivered through a first channel or lumen in a subcutaneous needle attached to the housing, to the openings in the wall of this needle, and may be simultaneously collected in the collecting vessel through a second lumen concentric with the first, for example, by means of the prevailing suction. An analyzing unit is installed adjacent to the drainage tube, i.e. as close as possible to the subcutaneous needle to be inserted into the tissue, which is used for determining the medical variable as well as the marker variable. In this way a fluid may be pumped through the subcutaneous needle for a short period of time, for instance, one minute or less, which may be re-collected after its partial equilibration. After a short interval the actual concentration of the substance of interest, such as blood sugar, may be indicated by a display unit or an acoustic alarm, which concentration is calculated by the analyzer from the concentration of the marker substance and that of the substance of interest. In order to obtain a uniform flow-rate during the time required for perfusion in the tissue various methods could be employed. For example, a uniform flow-rate may be achieved via a lever element whose lever is repeatedly actuated during the perfusion period. The lever may be returned into its initial position again and again by means of a spring or some other energy-storing element. The perfusion rate during the collecting period is in the range of 1 to 10 micro-liters per minute.

The only disadvantage of this device is the complex design of the part to be inserted into the tissue, in particular the high cost and technical difficulties involved in the manufacture of the multi-channel subcutaneous needle. Moreover, the diameter of such a needle must be kept comparatively large, which will cause the patient a certain amount of pain.

SUMMARY OF THE INVENTION

It is an object of the invention to propose a device which is based on the above state of the art, but is easier and less expensive to produce while it will retain the main advantages of its kind and minimize pain for the patient.

In the invention this object is achieved by configuring the part to be inserted into the tissue as a flexible plastic cannula with a puncturing needle on one end, and by providing that the two ends of the plastic cannula can be connected with feeder and drainage tubes of the delivery unit both on the pressure and suction side.

Instead of a multi-channel needle a comparatively thin plastic cannula is threaded through the skin and adjacent tissue of the patient, whose perforated part must be situated between the entrance and exit points of the puncturing needle, in order to prevent any loss of perfusion fluid or the admittance of air. After the needle has been inserted the end of the cannula is connected to the delivery unit of the device, which will permit continuous delivery of perfusion fluid through the plastic cannula, and the medical variable is measured in the manner referred to at the beginning of this paper, after partial equilibration of the perfusion fluid.

Both the puncturing needle and the single-channel plastic cannula may have very small cross-sections, which will cause the patient less discomfort.

For greater ease of handling of the device it is provided in an enhanced variant of the invention that the plastic cannula have a fixed stop in addition to a stop that may be slipped over the part of the plastic cannula emerging after the plastic cannula has been threaded through the tissue, the perforations of the exchange channel being situated between the two stops.

According to the invention the puncturing needle is attached to the plastic cannula by sealing, pressing or bonding, a smooth transition being provided from the puncturing needle to the plastic cannula. The needle may be fastened more securely by threading a thin wire through it, which is connected with the needle and is cut off along with it once the cannula has been threaded through the tissue. This will ensure that the needle and the cannula will remain connected during the puncturing process.

A further development of the invention provides that the end of the plastic cannula remote from the needle have a Luer connection which should be coupled to the feeder tube of the delivery unit, and that the other end should also be provided with a Luer connection, which should be coupled to the drainage tube of the delivery unit once the puncturing needle has been removed. In this way both ends of the plastic cannula may simply be plugged into the delivery unit of the device, i.e., the connection replacing the puncturing needle must be sealed or pressed on by the patient or doctor.

In an easy-to-handle variant of the invention the proposal is put forward that the needle end of the plastic cannula be inserted into an opening of the device after the needle has been removed, which opening should contain a gastight receiving element connecting to the drainage tube of the delivery unit, or rather, that the needle end of the plastic cannula be inserted into a receiving element of the drainage tube of the delivery unit together with the needle, the receiving element being provided with a pierceable septum.

The device of the invention could also have an automatic puncturing unit lifting a skin fold of constant thickness, possibly including a gun for painless puncture.

For mechanical cleaning of the exchange channel it is proposed in the invention that a mandrin be provided which should be introduced into the plastic cannula. By pushing a wire through the cannula any ingrowing tissue or tissue particles forcing their way into the cannula through the perforations in the exchange channel can be removed.

BRIEF DESCRIPTION OF THE DRAWINGS

Following is a more detailed description of the invention as illustrated by the attached drawings, in which FIG. 3 shows a variant of FIG. 1; and FIG. 4 shows a mandrin, partially in phantom, inserted into the plastic cannula according to the present invention.

DETAILED DESCRIPTION OF PREFERRED EMBODIMENTS

Figures 1, 2:
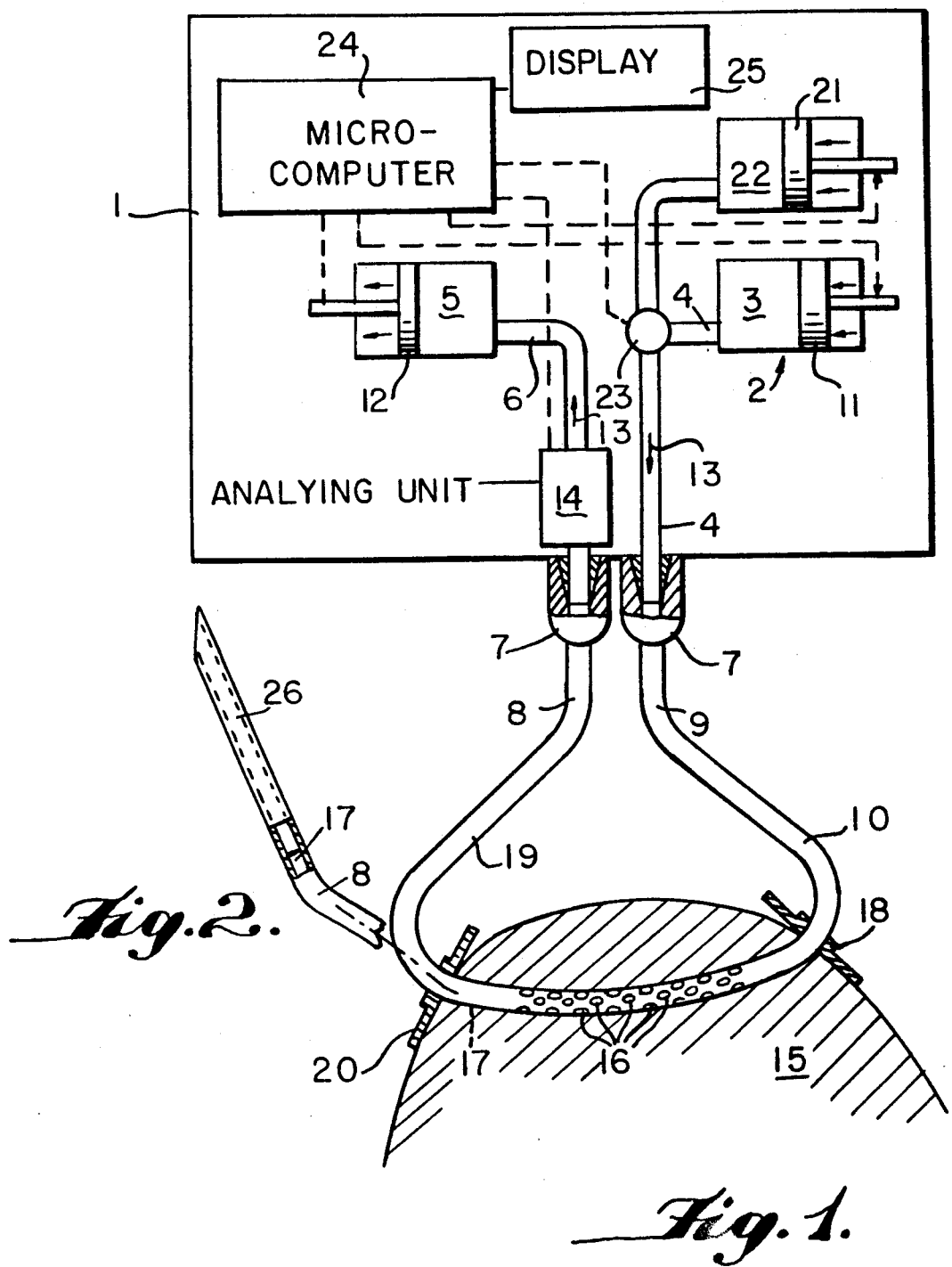
FIG. 1 presents a device of the invention to which a plastic cannula has been coupled.
FIG. 2 shows the plastic cannula from FIG. 1 including the puncturing needle.

The device shown schematically in FIG. 1 is provided with a delivery unit 2 located in a housing 1, which unit 2 essentially comprises a reservoir 3 for the perfusion fluid and a feeder tube 4 connected thereto, as well as a drainage tube 6 leading to a collecting vessel 5. The two tubes, 4 and 6, end on the outside of the housing 1 in Luer connections 7, the complementary parts of these connections holding the two ends, 8 and 9, of a plastic cannula 10 and connecting them to the delivery unit 2. The perfusion fluid may be induced to flow (cf. arrows 13) by means of a pressure element 11 located in the reservoir 3 or a suction element 12 in the collecting vessel 5. It is an advantage, of course, if both a pressure element 11 and a suction element 12 are provided, which is effected in a simple manner, i.e. by the use of a plunger pump, whose plunger chamber operates as a pressure pump and the space opening behind the plunger as a suction pump. Appropriate designs of a combined pressure and suction unit are described in WO 88/05643, as referred to at the beginning of this paper.

On the entrance end of the drainage tube 6 is located an analyzing unit 14 with sensors (not shown here) for measuring the medical variable and the marker variables. For example, the analyzing unit 14 may be provided with an ionic or conductivity sensor, a glucose sensor and a temperature sensor.

The part of the plastic cannula 10 situated in the tissue 15 has perforations 16 via which the perfusion fluid flowing through the the exchange channel 17 is in direct contact with the tissue. In order to prevent the plastic cannula 10 from slipping in the tissue it is arrested by a fixed stopping disk 18. After the cannula has been inserted the emerging part 19 also is provided with a movable stopping disk 20, which is slipped over this part.

The housing 1 may also contain a drug reservoir with a suitable pumping element 21, for instance, an insulin reservoir 22, which is connected to the feeder tube 4 via a multiway valve 23. The respective drug may be flushed into the tissue together with the perfusion fluid. The device is controlled by a microcomputer 24, which is connected, via signal and control leads, with the pressure and suction elements 11, 12, and the analyzing unit 14, as well as the pumping element 21 for the drug, and the multiway valve 23. Measurement readings and, possibly, the required dosage (i.e., unless the drug is administered automatically), are indicated via a display 25 connected to the microcomputer 24.

FIG. 2 shows in detail the puncturing needle 26 attached to the end 8 of the plastic cannula 10, which needle is removed or cut off after the cannula has been threaded through the tissue. The needle 26 and the plastic cannula 10 have the same diameter and are connected by sealing, pressing or bonding.

After removal of the puncturing needle 26 it is also possible to introduce the end 8 of the plastic cannula 10 into a receiving or gripping element in an opening of the housing 1, which is connected with the drainage tube.

FIG. 3 shows a variant in which the puncturing needle 26 remains on the plastic cannula 10 even after its insertion, and is introduced into a receiving element 28 provided with a pierceable septum 27. The receiving element 28 is in direct contact with the drainage tube 6, or rather, the analyzing unit 14.

FIG. 4 shows a mandrin 30 which has been almost completely inserted into the plastic cannula 10.

We claim:

1. A device for determining the concentration of at least one substance in organic tissue, comprising:
    a flexible plastic cannula, for insertion into said organic tissue, said cannula having an exchange channel with perforations, a feeder end having a feeder end connection and a drainage end having a drainage end connection;
    a delivery unit having a feeder tube comprising a connection which mates with the feeder end connection, said delivery unit providing a perfusion fluid which travels through said feeder end and into said exchange channel;
    an analyzing unit having a drainage tube which comprises a connection mating with said drainage end connection; and
    an evaluation unit connected to said delivery unit and said analyzing unit, said plastic cannula having a puncturing needle connected to one of said feeder end and said drainage end.

2. A device according to claim 1, wherein a smooth transition is provided from said puncturing needle to said plastic cannula.

3. A device according to claim 1, wherein said puncturing needle comprises said drainage end of said plastic cannula and said connection of said drainage tube, is provided with a pierceable septum for connection with said puncturing needle.

4. A device according to claim 1, wherein a mandrin is disposed within said exchange channel for mechanical cleaning of said exchange channel.

5. A device for determining the concentration of at least one substance in organic tissue, comprising:
- a flexible cannula inserted into said organic tissue, said cannula having a feeder end, a drainage end, and an exchange channel, said exchange channel having perforations between said feeder and drainage ends, said perforations being in contact with said tissue;
- a delivery means having a feeder tube connected to the feeder end of the plastic cannula for feeding a perfusion fluid through said feeder end into said exchange channel and into contact with said tissue through said perforations;
- a collecting vessel for draining said perfusion fluid from said drainage end after partial equilibration with said substance to be determined, where the degree of equilibration is indicated by one of endogenous and exogenous marker variables;
- an analyzing means for measuring the concentration of said substance to be determined and at least one of said marker variables, said analyzing means having drainage tube means for connecting to said drainage end and for connecting to said collecting vessel; and
- an evaluation means connected to the delivery unit, the collecting vessel and the analyzing means, said evaluation means for determining an actual concentration of said substance to be determined using at least one of said marker variables.

6. A device according to claim 5, wherein the feeder end of said plastic cannula has a Luer connection to be coupled to said feeder tube of said delivery unit, and wherein said drainage end of said plastic cannula is also provided with a Luer connection.

7. A device according to claim 5, wherein said substance to be determined is glucose and wherein at least one of the marker variables is a conductivity of said perfusion fluid.

8. A device according to claim 5, wherein said plastic cannula comprises a fixed stop at one of said feeder and drainage ends of said exchange channel, and a movable stop at the other of said feeder and drainage ends of said exchange channel, said movable stop being slipped over one of said feeder end and said drainage end of said plastic cannula after the same end has been threaded through said tissue, said perforations of said exchange channel being situated between said fixed and movable stops and held in contact with said tissue by said fixed and movable stops.

9. A device according to claim 5, wherein said exchange channel enters said tissue at one location and exits said tissue at a different location so that a loop is formed through said tissue.

* * * * *